United States Patent [19]
Janssen et al.

[11] Patent Number: 5,087,637
[45] Date of Patent: Feb. 11, 1992

[54] DIARYLACETYLENES, THE PREPARATION AND USE THEREOF

[75] Inventors: Bernd Janssen, Ludwigshafen; Hans-Heiner Wuest, Dossenheim, both of Fed. Rep. of Germany

[73] Assignee: BASF Aktiengesellschaft, Ludwigshafen, Fed. Rep. of Germany

[21] Appl. No.: 561,328

[22] Filed: Aug. 1, 1990

[30] Foreign Application Priority Data

Aug. 8, 1989 [DE] Fed. Rep. of Germany ....... 3926148

[51] Int. Cl.$^5$ ............................................ A61K 31/335
[52] U.S. Cl. ................................... 514/456; 514/772; 514/708; 514/710; 514/713; 514/825; 514/859; 514/861; 514/863
[58] Field of Search ................ 424/401; 514/510, 863, 514/772, 456, 708, 710, 713; 568/27, 28, 77, 38; 549/355, 398

[56] References Cited

U.S. PATENT DOCUMENTS

| 4,326,055 | 4/1982 | Loeliger | 542/429 |
|---|---|---|---|
| 4,806,558 | 2/1989 | Wuest et al. | 514/381 |
| 4,810,804 | 3/1989 | Chandraratna | 514/456 |
| 4,895,868 | 1/1990 | Chandraratna | 514/863 |
| 4,940,707 | 7/1990 | Klaus et al. | 514/708 |
| 4,994,489 | 2/1991 | Wuest et al. | 514/510 |

FOREIGN PATENT DOCUMENTS 1183541  3/1985  Canada .

OTHER PUBLICATIONS

Journal of the American Chemical Society, vol. 93, No. 12, 16 Jun. 1971, Gaston, PA, pp. 2974–2981; John J. Eisch et al., "Polar and Stereochemical Effects in the Addition of Triphenylaluminum to Para—substituted Diphenylacetylenes".

Primary Examiner—Thurman K. Page
Assistant Examiner—D. Colucci
Attorney, Agent, or Firm—Oblon, Spivak, McClelland, Maier & Neustadt

[57] ABSTRACT

Diarylacetylenes of the formula I

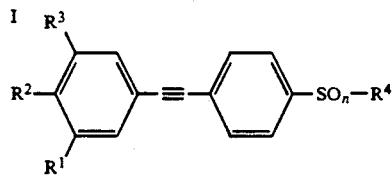

where $R^1$ is hydrogen or $C_1$–$C_4$-alkyl, $R^2$ and $R^3$ are each hydrogen or, when $R^1$ is hydrogen, together form a —C(CH$_3$)$_2$—B—C(CH$_3$)$_2$— group (where B is —CH$_2$Ch$_2$— or —CH(CH$_3$)—) or —OC(ch$_3$) (Z)CH$_2$CH$_2$— group (where Z is $C_1$–$C_2$-alkyl) or $R^2$ is $C_1$–$C_3$-alkoxy and $R^3$ is $C_1$–$C_{10}$-alkyl or, when $R^2$ is hydrogen, $R^1$ and $R^3$ are each alkyl as defined above, $R^4$ is $C_1$–$C_6$-alkyl and n is 0, 1 or 2, are prepared as described and used as active compounds in drugs and cosmetics.

18 Claims, No Drawings

DIARYLACETYLENES, THE PREPARATION AND USE THEREOF

The present invention relates to novel diaryl-substituted acetylenes, processes for the preparation thereof and the use thereof for the prophylaxis and control of diseases.

U.S. Pat. No. 4,326,055 and CA 1,183,541 disclose that retinoidal benzoic acid derivatives have pharmacological effects on topical and systemic treatment of neoplasms and dermatoses, e.g. acne or psoriasis. The disadvantage of these compounds is their low therapeutic index with regard to the side effects comprised by the term hypervitaminosis A.

It is also known that acetylene derivatives, as described in U.S. Pat. No. 4,806,558, have retinoidal effects, but these are not always satisfactory.

We have now found, surprisingly, that diarylacetylenes of the formula I

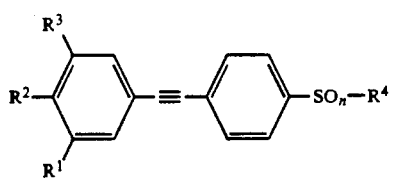

where $R^1$ is hydrogen or $C_1$-$C_4$-alkyl, $R^2$ and $R^3$ are each hydrogen or, when $R^1$ is hydrogen, together form a —C(CH$_3$)$_2$—B—C(CH$_3$)$_2$— group (where B is —CH$_2$CH$_2$— or —CH(CH$_3$)—) or —OC(CH$_3$)(Z)CH$_2$CH$_2$— group (where Z is $C_1$-$C_2$-alkyl) or $R^2$ is $C_1$-$C_3$-alkoxy and $R^3$ is $C_1$-$C_{10}$-alkyl which can be straight-chain, branched or (poly)cyclic, or, when $R^2$ is hydrogen, $R^1$ and $R^3$ are each alkyl as defined above, $R^4$ is $C_1$-$C_6$-alkyl and n is 0, 1 or 2, have a broad spectrum of action.

Preferred compounds of the formula I are those where $R^1$ and $R^3$ are each branched alkyl, and those where $R^2$ and $R^3$ together form a —C(CH$_3$)$_2$-B-C(CH$_3$)$_2$— group where B is particularly preferably —CH$_2$CH$_2$—.

Further preferred compounds of the formula I are those where $R^4$ is bonded to sulfinyl (n=1) or sulfonyl (n=2); sulfonyl is particularly preferred.

A compound according to the invention can be prepared by a) halogenating a stilbene of the formula II

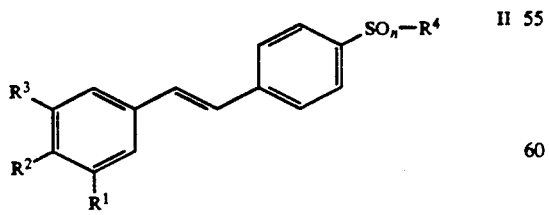

where $R^1$ to $R^4$ have the abovementioned meanings, and subsequently eliminating 2 moles of hydrogen halide, or b) reacting an α-chlorobenzylphosphonate of the formula III

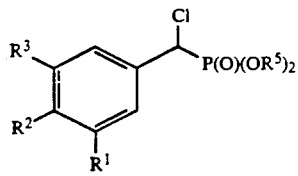

where $R^1$ to $R^3$ have the abovementioned meanings, and $R^5$ is $C_1$-$C_3$-alkyl, with an aldehyde of the formula IV

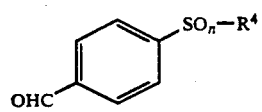

where $R^4$ has the abovementioned meanings, or c) reacting an α-chlorobenzylphosphonate of the formula V

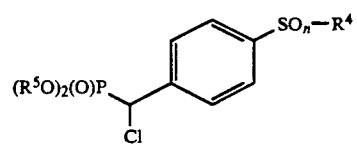

where $R^4$ and $R^5$ have the abovementioned meanings, with an aldehyde of the formula VI

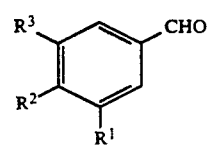

where $R^1$ to $R^3$ have the abovementioned meanings, or d) reacting a monoarylacetylene of the formula VII

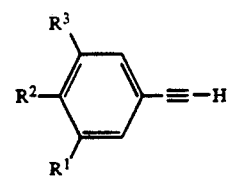

where $R^1$ to $R^3$ have the abovementioned meanings, with an aryl halide of the formula VIII

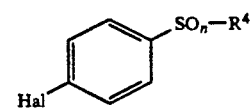

where $R^4$ has the abovementioned meanings, and Hal is chlorine, bromine or iodine, in the presence of a catalyst and of a base, or e) reacting an aryl halide of the formula IX

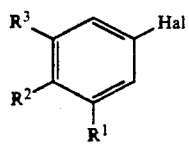

IX where $R^1$ to $R^3$ and Hal have the abovementioned meanings, with a monoarylacetylene of the formula X

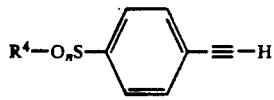

X where $R^4$ has the abovementioned meanings, in the presence of a catalyst and of a base,
and converting the resulting compound where appropriate by standard methods into another compound of the formula I.

Compounds of the formula II are halogenated in a) expediently with bromine in a solvent at up to 50° C., preferably in the range from −15° to 0° C. The solvents used are chlorinated hydrocarbons, especially chloroform or tetrachloromethane. In place of free bromine it is also possible to use complexes of molecular bromine with crown ethers, e.g. dibenzo-18-crown-6, or perbromides, e.g. tetrabutylammonium bromide.

Suitable bases for the elimination of two mole-equivalents of hydrogen bromide from the resulting dibromo compounds are the hydroxides, alcoholates, hydrides and amides of the alkali metals and alkaline earth metals. A solvent is expediently used.

It is also possible, if necessary, to exclude hydroxyl ions, e.g. with potassium tertbutanolate as base in tetrahydrofuran or dimethyl sulfoxide at from 25° to 60° C., or, particularly advantageously, in petroleum ether in the presence of a phase-transfer catalyst, preferably 18-crown-6, at the boiling point of the reaction mixture.

The compounds of the formula II can be prepared by the process described in DE-A 3,202,125, expediently by Wittig reaction of appropriate aromatic aldehydes with phosphonium salts or phosphonic esters.

The Wittig-Horner reactions b) and c) take place at up to 100° C., expediently at from 20° to 50° C. The reactions can be carried out under atmospheric pressure or in a closed vessel under elevated pressure, heating to the stated temperature range where appropriate.

These reactions can be carried out in the presence of a diluent or solvent, for example a lower saturated dialkyl ether, glycol dialkyl ether or cyclic ether, such as diethyl ether, ethyl tert-butyl ether, 1,2-dimethoxyethane, tetrahydrofuran or dioxane, an aromatic hydrocarbon such as benzene or an alkylbenzene such as toluene or xylene, or a saturated aliphatic hydrocarbon such as hexane, heptane or isooctane, a lower aliphatic ketone such as acetone, methyl ethyl ketone or methyl isobutyl ketone, or a dialkylformamide such as dimethyl- or diethylformamide, or in mixtures of the said solvents. Preferably used are cyclic ethers such as dioxane or tetrahydrofuran, and, in particular, dimethyl sulfoxide or mixtures thereof, the reaction generally taking place at up to 30° C.

The reactions are carried out in the presence of a deprotonating agent. Suitable for this are hydrides or amides of alkali metals, especially of sodium and potassium, the sodium and potassium salts of dimethyl sulfoxide, alkyllithium compounds such as n-butyllithium, or alkali metal alcoholates, preferably sodium methanolate or potassium tert-butanolate.

The overall reactions [b) and c)] (Wittig-Horner reaction + elimination) takes place particularly smoothly with 2 mole-equivalents of potassium tert-butanolate in dimethyl sulfoxide as solvent in a one-pot process (cf. J. Amer. Chem. Soc. 87 (1965), 2777).

In reactions d) and e), copper acetylides are prepared in situ from compounds of the formula VII and X, respectively, in a conventional manner and are reacted with the aryl halides VIII and IX, respectively, preferably the bromides or iodides, to give compounds of the formula I. Alternatively, the coupling reaction can be carried out directly on the acetylenes VII and X with catalysis by triphenylphosphine complexes of palladium or nickel. The presence of a base is expedient in all cases, for example an organic nitrogenous base such as triethylamine or pyridine, or an alkali metal alcoholate such as sodium methanolate or sodium phenolate. A solvent is used where appropriate, preferably dimethylformamide or tetrahydrofuran. The reaction takes place at from 50° to 150° C., expediently at 50° C. (aryl iodides) or 100° C. (aryl bromides).

It is advantageous where appropriate to use palladium compounds such as palladium acetate in amounts of from 0.1 to 10 mol %, in which case the reaction is carried out in a basic solvent such as triethylamine under atmospheric or superatmospheric pressure at up to 150° C., preferably at the reflux temperature of the solvent (cf. e.g.: Lambert Brandsma, "Preparative Acetylenic Chemistry", 2nd ed., Elsevier, Amsterdam 1988 and references cited therein).

The starting materials required for processes b, c, d and e can be obtained by known processes:

1-Aryl-1-chloromethylphosphonates of the formula III or V can be prepared, for example, by reacting in a conventional manner the appropriate aromatic aldehyde with a dialkyl phosphite, in the presence or absence of a catalytic amount of base, e.g. triethylamine or sodium methanolate or, particularly preferably, potassium tertbutanolate; the 1-aryl-1-hydroxymethylphosphonates prepared in this way are then treated in a conventional manner with thionyl chloride or phosphorus oxytrichloride and, where appropriate, in the presence of an acid acceptor such as pyridine or triethylamine.

The aldehydes of the formula IV or VI required for the Wittig-Horner reaction can be prepared, for example, by formylation of the corresponding benzene, tetralin or indane derivatives in the presence of a Lewis acid. The formylation is advantageously carried out with hexamethylenetetramine/trifluoroacetic acid. Tetrahydrotetramethylnaphthalene derivatives are described by T. F. Wood et al. in U.S. Pat. No. 3,442,640 and U.S. Pat. No. 3,499,751 or can be prepared by the processes indicated therein from 2,5-dichloro-2,5-dimethylhexane and an appropriately substituted benzene by Friedel-Crafts alkylation.

The monoarylacetylenes of the formula VII required as starting materials can be prepared as follows, for example an aryl methyl ketone of the formula XI

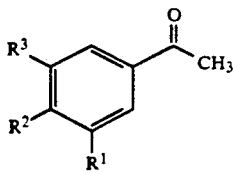

where $R^1$ to $R^3$ have the said meanings, is converted in a conventional manner with phosphorus pentachloride in the presence of a base such as pyridine at from 0° to 25° C. into the corresponding 1-aryl-1-chloroethylene which is converted with a base, preferably potassium tertbutanolate, in an aprotic dipolar solvent such as dimethyl sulfoxide at from 25° to 40° C. into the monoarylacetylene of the formula VII.

However, it is also possible to react an aldehyde of the formula VI with a phosphonium salt of the formula XI

$(Ar)_3 \ominus P—CH_2—Hal\ Hal\oplus$      XII where Ar is aryl, preferably phenyl, and Hal is chlorine, bromine or iodine, preferably bromine or chlorine, in a conventional Wittig reaction with base catalysis, and to dehydrohalogenate the resulting vinyl halide in situ with excess base to give the corresponding monoacetylene of the formula VII.

Most of the aryl halides of the formula VIII are known, or they can be prepared by conventional methods for halogenating aromatic compounds [cf. "Methoden der Organischen Chemie" (Houben-Weyl) Vol. 5/3, pp. 651 et seq., 4th ed. 1962; Vol. 5/4 pp. 233 et seq. and 354 et seq. and pp. 517 et seq., 4th ed. 1960].

Some of the aryl halides of the formula IX are known, or they can be prepared by the conventional halogenation processes indicated above.

Some of the acetylenes of the formula X are novel, and they are prepared by, for example, reacting an aldehyde of the formula IV with a phosphonium salt of the formula XII in accordance with the preparation of acetylenes VII.

The compounds of the general formula I, according to the invention, in which n is 0 can, if desired, be converted by conventional methods into the corresponding sulfoxides or sulfones.

The oxidation to sulfoxides is advantageously carried out by reacting the thioether in alcoholic solution with an equimolar amount or an up to 10% excess of periodic acid or an alkali metal salt thereof, preferably with its sodium salt, at from 0° to 30° C. Examples of suitable solubilizers are water, dimethyl sulfoxide or amides such as dimethylformamide, but also ketones such as acetone. The oxidation to sulfones is advantageously carried out by allowing 2 to 3 equivalents of the oxidizing agent to act on the appropriate thioether at from −30° to 120° C., preferably at from −10° to 60° C. Suitable oxidizing agents are hydrogen peroxide and, in particular, peroxycarboxylic acids, of which m-chloroperoxybenzoic acid is preferred. The preferred solvents are acetic acid or acetonitrile when hydrogen peroxide is used and are aprotic solvents such as methylene chloride or toluene when peroxycarboxylic acids are used.

Some of the novel compounds of the formula I contain chiral centers and are generally obtained as mixtures of diastereomers or racemates. The diastereomers can be separated and isolated in pure form, for example, by solubility differences or column chromatography. It is possible to obtain from pairs of enantiomers by known methods the pure enantiomers. The present invention embraces both the latter and mixtures thereof (racemates). Both the pure diastereomers or enantiomers and mixtures thereof can be used in therapy and cosmetics.

The compounds according to the invention and the physiologically tolerated salts thereof can, by reason of their pharmacological properties, be used for the topical and systemic therapy and prophylaxis of precanceroses and carcinomas of the skin, the mucous membranes and internal organs and for the topical and systemic therapy of acne, psoriasis and other dermatological disorders associated with pathological cornification, especially ichthyosis, Darier's disease, herpes, leukoplakia and for vitiligo, eczema, warts, damage from light (premature aging) of the skin, and for dry eyes and other corneopathies as well as for the treatment of rheumatic disorders, especially those of an inflammatory or degenerative nature affecting the joints, muscles, tendons and other parts of the locomotor system. Preferred indications are: the therapy of dermatological disorders; the therapy of skin damage caused by exposure to sunlight; the therapy of iatrogenic skin damage, e.g. atrophy induced by corticosteroids, and the prophylactic treatment of precanceroses and tumors.

The pharmacological effects can be demonstrated, for example, in the following test models: in hamster tracheal tissue in vitro the compounds according to the invention abolish the keratinization initiated by vitamin A deficiency. Keratinization is part of the early phase of carcinogenesis which, in a similar technique in vivo, is inhibited by the compounds of the formula I, according to the invention, after initiation by chemical compounds, by energetic radiation or after viral cell transformation. This method may be found in Cancer Res. 36 (1972), 964–972 or Nature 250 (1974), 64–66 and Nature 253 (1975), 45–50.

Furthermore, the compounds according to the invention inhibit the proliferation of certain cells with malignant changes. This method may be found in J. Natl. Cancer Inst. 60 (1978), 1035–1041, Experimental Cell Research 117 (1978), 15–22 and Proc. Natl. Acad. Sci. USA 77 (1980), 2937–2940.

The antiarthritic effect of the compounds according to the invention can be determined in a conventional animal experiment using the model of arthritis induced by adjuvant or by streptococcal cell wall. The dermatological activity, for example for the treatment of acne, can be detected, inter alia, by the comedolytic activity and the ability to reduce the number of cysts in the rhino mouse model.

This method is described by L. H. Kligman et al. in The Journal of Investigative Dermatology 73 (1978), 354–358. Another possible measure of the dermatological activity is the reduction in sebaceous glands and the associated reduction in sebum production by the flank organ of hamsters. This method is described by E. C. Gomez in J. Am. Ac. Dermatol. 6 (1982), 746–750.

In addition, the compounds according to the invention are able to bring about reversal of skin damage caused by UV light, and this can be determined in animal models. This method is described by L. H. Kligman et al. in Connect. Tissue Res. 12 (1984), 139–150 and in the Journal of the American Academy of Dermatology 15 (1986), 779–785.

Accordingly, the present invention also relates to cosmetics and therapeutics which are intended for topical and systemic use and contain a compound of the formula I in addition to conventional carriers or diluents.

These agents can be administered orally, parenterally or topically. Examples of suitable preparations are uncoated or (film-) coated tablets, capsules, pills, powders, solutions or suspensions, solutions for infusion or injection, and pastes, ointments, gels, creams, lotions, dusting powders, or emulsions and sprays.

The therapeutics or cosmetics can contain the compounds to be used according to the invention in a concentration of from 0.001 to 1%, preferably from 0.001 to 0.1%, for topical use, and preferably in a single dose of from 0.1 to 250 mg for systemic use in therapy, and can be administered in one or more doses each day depending on the nature and severity of the disorders.

The drugs and cosmetics of the present invention are prepared in a conventional manner with the conventional solid or liquid carriers or diluents is and the auxiliaries conventionally used in pharmaceutical technology, with a suitable dosage in accordance with the desired mode of administration.

Tablets can be obtained, for example, by mixing the active compound with conventional auxiliaries, for example inert diluents such as dextrose, sucrose, sorbitol, mannitol, polyvinylpyrrolidone, disintegrants such as corn starch or alginic acid, binders such as starch or gelatin, lubricants such as magnesium stearate or talc and/or agents to achieve a depot effect such as carboxypolymethylene, carboxymethylcellulose, cellulose acetate phthalate or polyvinyl acetate. The tablets can also be composed of several layers.

Correspondingly, coated tablets can be produced by coating cores, which have been produced in a manner similar to the tablets, with conventional coatings, e.g. polyvinylpyrrolidone or shellac, gum arabic, talc, titanium dioxide or sucrose. This coating can also be composed of several layers, and it is possible to use the auxiliaries mentioned above for tablets.

Solutions or suspensions of the active compound according to the invention can additionally contain flavorings such as saccharin, cyclamate or sucrose and, for example, vanillin or orange extract. They can also contain suspending auxiliaries such as sodium carboxymethylcellulose or preservatives such as p-hydroxybenzoates. Capsules containing active compounds can be produced, for example, by mixing the active compound with an inert carrier such as lactose or sorbitol and encapsulating in gelatin capsules.

Examples of appropriate conventional constituents of cosmetic and pharmaceutical preparations for topical use are: anionic, cationic and non-ionic emulsifiers and emulsion stabilizers, which can also provide texture or form gels, such as polyvinylpyrrolidone, fatty alcohols, glycerol monostearate, polyacrylic acids, cellulose derivatives and ethylene oxide/propylene oxide block copolymers, solid or liquid oily components or fats of mineral, vegetable or animal origin, synthetic ester oils such as triglycerides and isopropyl myristate, hydrophilic components such as glycerol, polyethylene glycol and propylene glycol.

Examples of other ingredients of cosmetics which may be mentioned are sunscreen agents, sun tan agents, preservatives, antioxidants, pigments, colorants, essential oils and perfume oils, vitamins, plant extracts, collagen etc. These substances are to be found, for example, in the CTFA Cosmetic Ingredient Dictionary, 3rd edition, Washington 1982.

The examples and methods which follow explain the preparation of the novel compounds and precursors thereof:

Preparation of the starting compounds

EXAMPLE A 3,5-Di-tert-butylphenylacetylene 73.7 g (0.655 mol) of potassium tert-butanolate were added a little at a time to 117.6 g (0.269 mol) of bromomethyltriphenylphosphonium bromide in 420 ml of dry tetrahydrofuran at 25° C. while cooling. The reaction mixture was then stirred for half an hour and, at −70° C., a solution of 50 g (0.218 mol) of 3,5-di-tert-butylbenzaldehyde in 120 ml of dry tetrahydrofuran was added dropwise. After half an hour, the mixture was allowed to warm to room temperature, and was then stirred overnight and poured into water. Extraction with ether, washing of the organic phase with water, drying over sodium sulfate and evaporation of the solvent produced a viscous residue.

Distillation provided 18.7 g of the title compound.

Boiling point: 90°–94° C. (0.2 mmHg) $^1$H-NMR (CDCl$_3$): δ=1.3 (s, 18H); 3.05 (s, H); 7.4 (m, 3H)

EXAMPLE B

4-Methylsulfonylbromobenzene 102.4 ml of hydrogen peroxide (30% strength) were added to 40.6 g (0.2 mol) of 4-bromothioanisole in 300 ml of glacial acetic acid at 50° C. within one hour. After the reaction was complete, the solution was poured into ice-water, and the precipitate was filtered off with suction, washed with water and dried under reduced pressure.

42 g of the title compound of melting point 102°–104° C. were obtained. Synthesis of the products

EXAMPLE 1

2-(5,6,7,8-Tetrahydro-5,5,8,8-tetramethyl-2-naphthyl)-1-(4-methylsulfonylphenyl)acetylene 3.2 g (0.015 mol) of 5,6,7,8-tetrahydro-5,5,8,8-tetramethyl-2-naphthylacetylene, 3 g (0.0128 mol) of 4-methylsulfonylbromobenzene, 12.7 g (0.126 mol) of triethylamine, 12.3 mg (0.047 mmol) of triphenylphosphine, 1.9 mg (0.0027 mmol) of bis(triphenylphosphine)-palladium(II) chloride and 6.5 mg (0.034 mmol) of copper(I) iodide in 4 ml of dry dimethylformamide were refluxed under nitrogen. After the reaction was complete, the cooled mixture was poured into water, and the mixture was adjusted to pH 5 with dilute hydrochloric acid and extracted with ether. The organic phase was washed with water, dried over sodium sulfate and evaporated to give 5.5 g of a residue which was recrystallized from methanol to provide 3.5 g of the title compound. Melting point: 153°–155° C.

The following were obtained by procedures similar to that described in Example 1.

EXAMPLE 2

2-(5,6,7,8-Tetrahydro-5,5,8,8-tetramethyl2-naphthyl)-1-(4-ethylsulfonylphenyl)acetylene, melting point 166°–168° C., from 5,6,7,8-tetrahydro-5,5,8,8-tetramethyl-2-naphthylacetylene and 4-ethylsulfonylbromobenzene.

EXAMPLE 3

2-(5,6,7,8-Tetrahydro-5,5,8,8-tetramethyl2-naphthyl)-1-(4-isopropylsulfonylphenyl)acetylene, melting point 152°–153° C., from 5,6,7,8-tetrahydro-5,5,8,8-tetramethyl-2-naphthylacetylene and 4-isopropylsulfonylbromobenzene.

EXAMPLE 4

1-(3,5-Di-tert-butylphenyl)-2-(4-ethylsulfonylphenyl)acetylene, melting point 136°–137° C., from 3,5-di-tert-butylphenylacetylene and 4-ethylsulfonylbromobenzene.

EXAMPLE 5

2-(5,6,7,8-Tetrahydro-5,5,8,8-tetramethyl-2-naphthyl)-1-(4-methylthiophenyl)acetylene 4.0 g (18.9 mmol) of 5,6,7,8-tetrahydro-5,5,8,8-tetramethyl-2-naphthylacetylene dissolved in 40 ml of triethylamine were added dropwise to a boiling solution of 3.2 g (15.8 mmol) of 4-bromothioanisole, 35.5 mg (0.15 mmol) of palladium(II) acetate, 1.7 g (6.5 mmol) of triphenylphosphine and 120 mg (0.6 mmol) of copper(I) iodide in 80 ml of triethylamine. After the reaction was complete, the precipitate was removed, the filtrate was evaporated and the residue was digested with heptane.

1.0 g of the title compound of melting point 120°–123° C. was obtained.

The Examples indicated in the following table were prepared in a similar manner:

TABLE

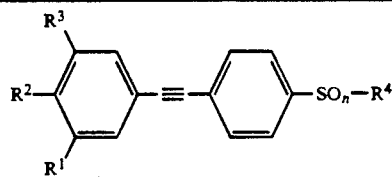

I

| Ex. No. | $R^1$ | $R^3$ | $R^4$ | mp. |
|---|---|---|---|---|
| 6 | $-C(CH_3)_2-CH_2CH_2-C(CH_3)_2-$ | H | $-SOCH_3$ | |
| 7 | $-C(CH_3)_2-CH_2CH_2-C(CH_3)_2-$ | H | $-SC(CH_3)_3$ | |
| 8 | $-C(CH_3)_2-CH_2CH_2-C(CH_3)_2-$ | H | $-SO_2C(CH_3)_3$ | |
| 9 | $-C(CH_3)_2-CH_2CH_2-C(CH_3)_2-$ | H | $-S-C_6H_{11}$ | |
| 10 | $-C(CH_3)_2-CH_2CH_2-O$ | H | $-SO_2CH_3$ | |
| 11 | $-C(CH_3)_3$ | $-C(CH_3)_3$ | $-SOC_2H_5$ | |
| 12 | H | $C_{10}H_{15}$ | $-SO_2CH_3$ | |
| 13 | $-CH(CH_3)_2$ | $-CH(CH_3)_2$ | $-SO_2C_2H_5$ | |

Examples of pharmaceutical preparations:

EXAMPLE 1

Tablet containing 250 mg of active compound

| Composition for 1,000 tablets: | |
|---|---|
| Active compound of Example No. 2: | 250 g |
| Potato starch: | 100 g |
| Lactose: | 50 g |
| 4% Gelatin solution: | 45 g |
| Talc: | 10 g |

Production

The finely powdered active compound, potato starch and lactose are mixed. The mixture is moistened with about 45 g of 4% gelatin solution and converted into fine granules, which are dried. The dried granules are screened, mixed with 10 g of talc and compressed to tablets in a rotary tabletting machine. The tablets are packed into polypropylene containers which are tightly closed.

EXAMPLE II

Cream containing 0.1% active compound

| Active compound of Example No. 7: | 0.1 g |
|---|---|
| Glycerol monostearate: | 10.0 g |
| Cetyl alcohol: | 4.0 g |
| Polyethylene glycol 400 stearate: | 10.0 g |
| Polyethylene glycol sorbitan monostearate: | 10.0 g |
| Propylene glycol: | 6.0 g |
| Methyl p-hydroxybenzoate: | 0.2 g |
| Demineralized water: | ad 100.0 g |

Production

The active compound is very finely powdered and suspended in propylene glycol, and the suspension is stirred into a melt of the glycerol monostearate, cetyl alcohol, polyethylene glycol 400 stearate and polyethylene glycol sorbitan monostearate at 65° C. This mixture is converted into an emulsion with an aqueous solution of the methyl p-hydroxybenzoate at 70° C. The cream is cooled and then homogenized in a colloid mill and packed in tubes.

EXAMPLE III

Dusting powder containing 0.1% active compound

| Active compound of Example No. 4: | 0.1 g |
|---|---|
| Zinc oxide: | 10.0 g |
| Magnesium oxide: | 10.0 g |
| Highly disperse silica: | 2.5 g |
| Magnesium stearate: | 1.0 g |
| Talc: | 76.4 g |

Production

The active compound is micronized in an air jet mill and mixed homogeneously with the other ingredients. The mixture is forced through a screen (mesh no. 7) and packed in polyethylene containers with sprinkler top.

We claim:

1. A diarylacetylene of the formula I

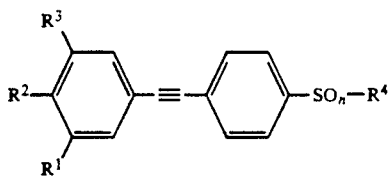

where $R^1$ is hydrogen or $C_1$-$C_4$-alkyl, $R^2$ and $R^3$ are each hydrogen or, when $R^1$ is hydrogen, together form a —C(CH$_3$)$_2$—B—C(CH$_3$)$_2$— group where B is —CH$_2$CH$_2$— or —CH(CH$_3$)— or an —OC(CH$_3$)(Z)CH$_2$CH$_2$— group where Z is $C_1$-$C_2$-alkyl or $R^2$ is $C_1$-$C_3$-alkoxy and $R^3$ is $C_1$-$C_{10}$-alkyl or, when $R^2$ is hydrogen, $R^1$ and $R^3$ are each alkyl as defined above, $R^4$ is $C_1$-$C_6$-alkyl and n is 0, 1 or 2.

2. A diarylacetylene of the formula I as claimed in claim 1, where $R^2$ and $R^3$ together form a —C(CH$_3$)$_2$—B—C(CH$_3$)$_2$— group.

3. A diarylacetylene of the formula I as claimed in claim 1, where $R^1$ and $R^3$ are each $C_1$-$C_4$-alkyl.

4. A diarylacetylene of the formula I as claimed in claim 2, where n is 2.

5. A diarylacetylene of the formula I as claimed in claim 1, where $R^3$ is adamantyl and $R^2$ is $C_1$-$C_3$-alkoxy.

6. A process for the preparation of a diarylacetylene of the formula I as claimed in claim 1, which comprises
a) halogenating a stilbene of the formula II

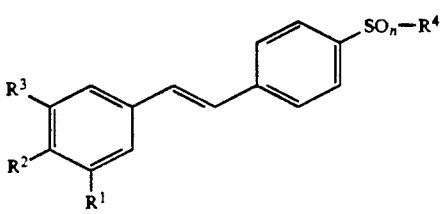

where $R^1$ to $R^4$ and n have the meanings specified in claim 1, and subsequently eliminating 2 moles of hydrogen halide, or b) reacting an α-chlorobenzylphosphonate of the formula III

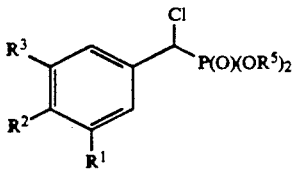

where $R^1$ to $R^3$ have the abovementioned meanings, and $R^5$ is $C_1$-$C_3$-alkyl, with an aldehyde of the formula IV

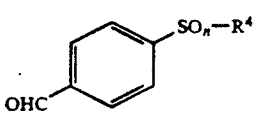

where $R^4$ and n have the meanings specified in claim 1, or c) reacting an α-chlorobenzylphosphonate of the formula V

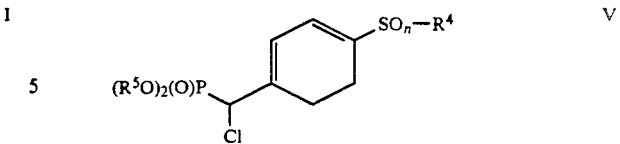

where $R^4$, $R^5$ and n have the abovementioned meanings, with an aldehyde of the formula VI

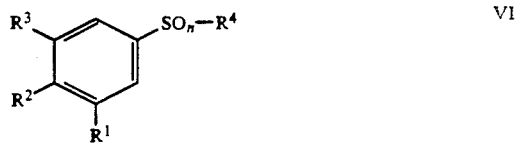

where $R^1$ to $R^3$ have the abovementioned meanings, or d) reacting a monoarylacetylene of the formula VII

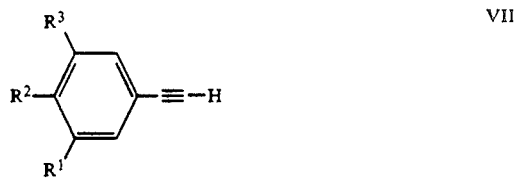

where $R^1$ to $R^3$ have the abovementioned meanings, with an aryl halide of the formula VII

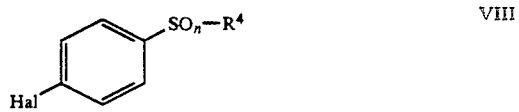

where $R^4$ and n have the abovementioned meanings, and Hal is chlorine, bromine or iodine, in the presence of a catalyst and of a base, or e) reacting an aryl halide of the formula IX

where $R^1$ to $R^3$ and Hal have the abovementioned meanings, with a monoarylacetylene of the formula X

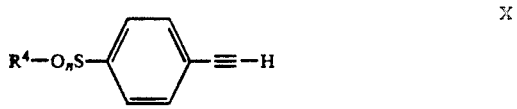

where $R^4$ has the abovementioned meanings, in the presence of a catalyst and of a base and converting the resulting compound into a compound of formula I'' followed by a period ..

7. A cosmetic preparation for topical application which comprises a cosmetically effective amount of the diarylacetylene compound of formula I as claimed in claim 1 in combination with a cosmetically acceptable carrier.

8. The cosmetic preparation of claim 7, which contains from 0.001 to 1% by weight of said diarylacetylene compound.

9. A pharmaceutical composition for topical application which comprises: a therapeutically effective amount of the compound of formula I of claim 1 in combination with a therapeutically acceptable carrier.

10. The pharmaceutical composition of claim 9, wherein the amount of said active diarylacetylene compound ranges from 0.001 to 1% by weight.

11. A pharmaceutical composition for systemic application, which comprises: a therapeutically effective amount of the diarylacetylene of formula I of claim 1 in combination with a therapeutically acceptable carrier.

12. The composition of claim 11, wherein the amount of said active diarylacetylene compound ranges from 0.1 to 250 mg per single dose of the composition.

13. A method of treating acne, psoriasis or other dermatological disorders associated with pathological cornification and of eczema, warts and vitiligo, comprising: applying to the desired area of the skin the composition of claim 9.

14. A method of treating skin damage which is iatrogenic or caused by UV light, comprising: treating the area of the skin which is damaged with the pharmaceutical composition of claim 9.

15. A method of treating precanceroses and tumors, comprising: applying to the affected area of the skin the pharmaceutical composition of claim 9.

16. A method of treating precanceroses and tumors, comprising: administering a therapeutically effective amount of the composition of claim 11 to a subject.

17. A method of treating rheumatic and arthritic disorders, comprising: applying a therapeutically effective amount of the composition of claim 9 to the desired areas of the skin.

18. A method of treating rheumatic and arthritic disorders, which comprises: administering to a subject a therapeutically effective amount of the composition of claim 11.

* * * * *